United States Patent [19]
Pilgram

[11] 3,966,817
[45] June 29, 1976

[54] HERBICIDAL ORTHO-NITROANILINES

[75] Inventor: Kurt H. G. Pilgram, Modesto, Calif.

[73] Assignee: Shell Oil Company, Houston, Tex.

[22] Filed: Mar. 25, 1974

[21] Appl. No.: 454,185

[52] U.S. Cl. .................................. 260/578; 71/103
[51] Int. Cl.² ........................................ C07C 87/50
[58] Field of Search .................................. 260/578

[56] References Cited
UNITED STATES PATENTS

| | | | |
|---|---|---|---|
| 3,551,500 | 12/1970 | Model et al. | 260/578 X |
| 3,576,872 | 4/1971 | Singhal | 260/578 X |
| 3,632,582 | 1/1972 | Bill | 260/578 X |
| 3,634,478 | 1/1972 | Halasz et al. | 260/578 X |

*Primary Examiner*—Paul F. Shaver

[57] ABSTRACT

Ortho-nitroanilines of the formula

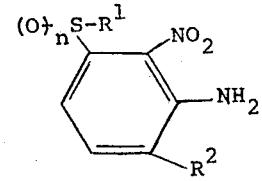

wherein the symbols have the respective meanings set forth in the specification hereinafter, and their use as herbicides.

2 Claims, No Drawings

HERBICIDAL ORTHO-NITROANILINES

DESCRIPTION OF THE INVENTION

It has been found that high levels of herbicidal activity are characteristic of o-nitroanilines of formula (I) wherein a. $R^1$ is methyl, $R^2$ is chlorine and $n = 0$, 1 or 2;
b. $R^1$ is ethyl, $R^2$ is chlorine and $n = 1$;
c. $R^1$ is propyl, $R^2$ is chlorine or methyl and $n = 1$;
d. $R^1$ is iso-butyl, $R^2$ is chlorine or methyl and $n = 0$, 1 or 2.

Highest activity appears to be characteristic of that sub-class wherein $R^1$ is isobutyl and $R^2$ is chlorine; accordingly this sub-class is a preferred embodiment of the invention.

The preparation of the o-nitroanilines of this invention is described in the following examples. In all cases, the identity of the product, and of any intermediate involved, was confirmed by elemental analysis and by infrared and nuclear magnetic resonance spectrum analyses.

EXAMPLE 1

6-chloro-3-isobutylthio-2-nitroaniline

A solution of sodium isobutylmercaptide was prepared by dissolving 4.3 g of sodium in 200 ml of ethanol, followed by the addition of 16.7 g of isobutylmercaptan, concentrating under vacuum and dissolving the residual white solid in 200 ml of dimethyl sulfoxide. The solution was added with stirring, to a solution of 35 g of 3,6-dichloro-2-nitroaniline in 200 ml of dimethyl sulfoxide. The mixture was stirred at 45° for 15 minutes, then was poured into 1000 ml of water. The crude product was collected by filtration and dried to give 43.4 g of 1 as a red crystalline solid, m.p.: 64°–65°.

By the same general procedure was prepared:

EXAMPLE 2

6-chloro-3-(methylthio)-2-nitroaniline

As a red solid, m.p.: 89°–90°.

EXAMPLE 3

5-(isobutylthio)-6-nitro-o-toluidine

As a red solid, m.p.: 79°–89°.

EXAMPLE 4

6-chloro-3-(isobutylsulfinyl)-2-nitroaniline

A solution of 12.5 g of 81% meta-chlorperbenzoic acid in 100 milliliters of chloroform was added gradually at ambient temperature to a stirred solution of 15 g of (I) in 50 ml of chloroform. After 1 hour, the reaction mixture was washed well with 5% aqueous sodium carbonate, and with water, dried and concentrated to dryness. The residual solid crystallized from ether-hexane to give 15.1 g of 4 as a yellow crystalline solid, m.p.: 111°–112°.

In a similar manner there was prepared:

EXAMPLE 5

6-chloro-3-(methylsulfinyl)-2-nitroaniline

Prepared from 2 as a yellow-brown solid, m.p.: 151°–153°.

EXAMPLE 6

5-(isobutylsulfinyl)-6-nitro-o-toluidine

Prepared from 3 as a yellow-brown solid, m.p.: 126°–127°.

In the following three examples, the alkylthio precursor was prepared by the general procedure of Example 1, then oxidized by the general procedure of Example 4.

EXAMPLE 7

6-chloro-3-(ethylsulfinyl)-2-nitrobenzenamine

As an orange solid, m.p.: 101°–105°.

EXAMPLE 8

6-chloro-2-nitro-3-(propylsulfinyl)benzenamine

As an orange solid, m.p.: 117°–119°.

EXAMPLE 9

6-methyl-2-nitro-3-(propylsulfinyl)benzenamine

As an orange solid, m.p.: 110°–114°.

EXAMPLE 10

6-chloro-3-(isobutylsulfonyl)-2-nitroaniline

A solution of 25 g of 81% meta-chloroperbenzoic acid in 150 ml chloroform was added to a solution of 15 g of 1 in 100 ml of chloroform. The solution was heated to reflux for 1 hour, cooled, washed with 5% aqueous sodium carbonate, and water, dried and concentrated to dryness. The residual solid crystallized from methanol to give 13.4 g of 10 as a yellow crystalline solid, m.p.: 102°–104°.

EXAMPLE 11

6-chloro-3-(methylsulfonyl)-2-nitroaniline

A solution of 21.8 g of 2 in 250 ml of glacial acetic acid containing 40 g of 33% hydrogen peroxide was heated for 15 minutes to 95°–100° in a steam bath. The reaction mixture then was poured into ice water and the mixture filtered. Recrystallization of the solid from methanol gave 19.1 g of 11 as a yellow crystalline solid, m.p.: 126°–129°.

EXAMPLE 12

5-(isobutylsulfonyl)-6-nitro-o-toluidine

Was prepared from 3 according to the procedure of Example 10 as a yellow solid, m.p.: 109°–111°.

Compounds of this invention have been found to be herbicidally effective with regard to a variety of plant species, including economically important species of grasses and broad-leaved weeds. They have been found to be active by pre-emergence application (applied to the soil prior to germination of the plant seeds) and by post-emergence application (applied to the foliage of the plant).

Accordingly, herbicidal compositions of this invention comprise at least one nitroaniline of Formula I and an inert agriculturally acceptable carrier therefor. Undesirable plant growth is destroyed or prevented by applying an effective amount of at least one of the nitroanilines of Formula I ordinarily in a herbicidal composition of one of the types described hereinafter to either the unwanted vegetation itself or to the area to be kept free of such unwanted vegetation.

The amount of nitroaniline required for controlling unwanted plants will naturally depend upon the variety or varieties of plants involved, whether the herbicide is to be applied pre-emergence or post-emergence, the kind and condition of the soil (if applied pre-emergence) or the age and condition of the plants (if applied post-emergence), the degree of control desired, the character of the formulation used, the mode of application, the climate, the season of the year and other variables which must be and are taken into account by practitioners of the art of chemical control of unwanted plants. Recommendation as to precise dosages is therefore not possible. In general, however, when applied pre-emergence to a locus to be protected, dosages of from about 0.1 to about 10 pounds per acre of the nitroaniline will be satisfactory. When applied post-emergence, the usual practice is to spray or dust the foliage of the plants to apply the needed dosage to the foliage. The nominal dosage in this case also is from about 0.1 to about 10 pounds per acre of the nitroaniline. Liquid and dust formulations for such application ordinarily contain from about ½ to 10% of the nitroaniline.

The nitroaniline may be formulated as a wettable powder, a dust, as granules, as a solution, as an emulsifiable concentrate, emulsion, suspension concentrate or aerosol. Wettable powders are usually compounded to contain from about 25% to about 75% by weight of toxicant and usually contain in addition to solid carrier, 3–10% by weight of a dispersing agent and, where necessary, up to 10% by weight of stabilizer(s) and/or other additives such as penetrants or stickers. Dusts are usually formulated as a concentrate having a similar composition to that of a wettable powder but without a dispersant, and are diluted in the field with further solid carrier to give a composition usually containing ½–10% by weight of toxicant. Generally, granules will contain ½–25% by weight toxicant and 0–10% by weight of additives such as stabilizers, slow release modifiers and binding agents. Any of the solid materials commonly used for formulating agricultural chemicals can be used. Examples include: talc, clays, pumice, diatomaceous earth, silica, walnut granules and flour, chalk and the like. Emulsifiable concentrates usually contain, in addition to the solvent and, when necessary, co-solvent, 10–50% weight per volume toxicant, 2–20% weight per volume emulsifiers and 0–20% weight per volume of appropriate additives such as stabilizers, penetrants and corrosion inhibitors. Suitable solvents include xylene, toluene, acetone, methanol, 2-butanone, cellosolve, isopropanol, chlorol, butanol, acetonitrile.

Suspension concentrates are compounded so as to obtain a stable, non-sedimenting flowable product and usually contain 10–75% by weight of toxicant, 0.5–15% by weight of dispersing agents, 0.1–10% by weight of suspending agents such as protective colloids and thixotropic agents, 0–10% by weight of appropriate additives such as defoamers, corrosion inhibitors, stabilizers, penetrants and stickers, and as carrier, water or an organic liquid in which the toxicant is substantially insoluble; certain organic solids or inorganic salts may be dissolved in the carrier to assist in preventing sedimentation or as antifreeze agents for water.

Aqueous dispersions and emulsions of these formulations are obtained by diluting such wettable powders or concentrates with water. The said emulsions may be of the water-in-oil or of the oil-in-water type, and may have a thick mayonnaise-like consistency.

The compositions containing the nitroaniline may also contain other ingredients, for example, other compounds possessing pesticidal, expecially insecticidal, acaricidal, herbicidal or fungicidal properties.

The pre-emergence herbicidal activity of the compounds of the invention was evaluated by planting seeds of watergrass and cress in test tubes nominally measuring 25 × 200 millimeters, containing soil treated with the test compounds at the rate of 0.1 and 1 milligrams of the active compound per tube designated in Table II as Rates I and II, respectively. The planted soil was held under controlled conditions of temperature, moisture, and light for 13 to 14 days. The amount of germination was then noted and the effectiveness of the test compound was rated on the basis of an 0 to 9 scale, 0 rating indicating no effect and 9 indicating death of the seedlings or no germination.

The post-emergence activity of the compounds of this invention was evaluated by spraying 10-day old pigweed plants and 7-day old crabgrass plants to runoff with a liquid formulation of the test compound at the rates of 0.62 milliliters of an 0.04% solution designated Rate I in Table I and 0.56 milliliters of an 0.5% solution designated Rate I in Table I. The sprayed plants were held under controlled conditions for 10 to 11 days and the effect of the test chemical then evaluated visually, the results being rated on the 0 to 9 scale described above.

The results of the tests are summarized in Table I.

TABLE I

| | HERBICIDAL ACTIVITY | | | | | | | |
|---|---|---|---|---|---|---|---|---|
| | Pre-Emergence | | | | Post-Emergence | | | |
| Compound | Watergrass | | Cress | | Crabgrass | | Pigweed | |
| of Example | Rate I | Rate II | Rate I | Rate II | Rate I | Rate II | Rate I | Rate II |
| 1 | 2 | 3 | 6 | 9 | 5 | 9 | 9 | 9 |
| 2 | 1 | 9 | 2 | 9 | 7 | 9 | 9 | 9 |
| 3 | 0 | 2 | 0 | 9 | 5 | 9 | 7 | 9 |
| 4 | 9 | 9 | 9 | 9 | 0 | 9 | 9 | 9 |
| 5 | 3 | 8 | 7 | 9 | 3 | 9 | 9 | 9 |
| 6 | 9 | 9 | 9 | 9 | 6 | 9 | 7 | 9 |
| 7 | 4 | 8 | 4 | 9 | 7 | 8 | 8 | 9 |
| 8 | 3 | 7 | 9 | 9 | 8 | 9 | 8 | 9 |
| 9 | 1 | 7 | 8 | 9 | 7 | 8 | 8 | 9 |
| 10 | 5 | 8 | 9 | 9 | 5 | 8 | 6 | 9 |
| 11 | 1 | 6 | 3 | 9 | 6 | 7 | 5 | 9 |
| 12 | 3 | 8 | 6 | 8 | 0 | 9 | 5 | 9 |

The herbicidal activity of compounds of this invention was determined with respect to several common species of weeds by spraying a formulation of the test compound onto the soil in which the weed seeds had been planted (pre-emergence test) or onto the foliage of the plants (post-emergence tests). In each series of tests, the soil was held in containers that isolated that soil into a narrow band or row. The solution of test chemical was sprayed over the band from one end to the other, the concentration of the test compound in the formulation varying logarithmically from a higher value at one end of the band to a lower value at the other end of the band. The effect of the test chemical was evaluated visually and reported as the nominal rate of application, in pounds of test chemical per acre of the soil band, at which 90% inhibition of the growth of the weeds occurred, this being referred to as the 90% growth inhibition or $GI_{90}$ dosage. Results of the pre-emergence tests, as well as the weed species involved, are set out in Table III while similar data for the post-emergence tests are set out in Table IV.

Table II

| | PRE-EMERGENCE TESTS WEED SPECIES | | | | | |
|---|---|---|---|---|---|---|
| Compound of Example | Cheatgrass | Crabgrass | Watergrass | Pigweed | Mustard | Curley Dock |
| 1 | >2.8 | 0.5 | 2.8 | <0.5 | >2.8 | <0.5 |
| 2 | — | 0.7 | 2.3 | <0.5 | 1.7 | — |
| 3 | >2.8 | 0.7 | >2.8 | <0.5 | >2.8 | <0.5 |
| 4 | 1.6 | 0.9 | >2.8 | <0.5 | 1.6 | 0.9 |
| 5 | >2.8 | <0.5 | 2.1 | 0.5 | 2.1 | 1.6 |
| 6 | 2.1 | 0.5 | 2.1 | <0.5 | >2.8 | <0.5 |
| 7 | >2.8 | 0.7 | 2.1 | <0.5 | 0.9 | 1.8 |
| 8 | >2.8 | 0.9 | >2.8 | 0.5 | 1.6 | 0.7 |
| 9 | >2.8 | 1.4 | >2.8 | <0.5 | >2.8 | <0.5 |
| 10 | >2.8 | 1.6 | >2.8 | <0.5 | 2.1 | <0.5 |
| 11 | — | 2.3 | >3.0 | 0.5 | >3.0 | — |
| 12 | 2.8 | 2.1 | >2.8 | <0.5 | >2.8 | 0.6 |

Table III

| | POST-EMERGENCE TESTS WEED SPECIES | | | | | |
|---|---|---|---|---|---|---|
| Compound of Example | Cheatgrass | Crabgrass | Watergrass | Pigweed | Mustard | Curly Dock |
| 1 | >5 | 1.6 | >5 | <0.5 | 3.8 | 1.6 |
| 2 | >5 | 0.7 | 4.4 | <0.5 | 2.5 | 3.3 |
| 3 | >5 | >5 | >5 | <0.5 | 3.8 | 1.6 |
| 4 | >5 | 3.8 | >5 | 1.6 | >5 | 2.8 |
| 5 | 2.8 | 1.8 | >5 | <0.5 | 1.2 | 2.1 |
| 6 | >5 | 2.1 | >5 | <0.5 | >5 | 0.5 |
| 7 | >5 | 2.1 | >5 | 0.9 | 1.6 | 2.5 |
| 8 | >5 | 1.8 | >5 | 1.2 | 2.8 | 1.6 |
| 9 | >5 | >5 | >5 | 0.9 | >5 | 2.1 |
| 10 | >5 | >5 | >5 | 3.8 | >5 | >5 |
| 11 | >5 | 3.3 | >5 | <0.5 | >5 | 3.8 |
| 12 | — | — | — | — | — | — |

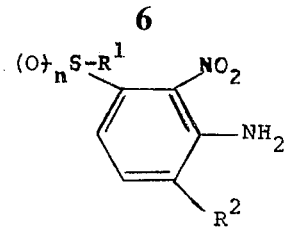

wherein
a. $R^1$ is methyl, $R^2$ is chlorine and $n = 0$, 1 or 2;
b. $R^1$ is ethyl, $R^2$ is chlorine and $n = 1$;
c. $R^1$ is propyl, $R^2$ is chlorine or methyl, and $n = 1$; and
d. $R^1$ is iso-butyl, $R^2$ is chlorine or methyl and $n = 0$, 1 or 2.

I claim as my invention:
1. An o-nitroaniline of the formula:

2. An o-nitroaniline according to claim 1 wherein $R^1$ is isobutyl and $R^2$ is chlorine.

* * * * *